(12) United States Patent
Kluesener et al.

(10) Patent No.: US 8,748,646 B2
(45) Date of Patent: Jun. 10, 2014

(54) PROCESS OF MAKING β-HYDROXYAMINO COMPOUNDS

(75) Inventors: Bernard William Kluesener, Harrison, OH (US); Robert Edward Shumate, Hamilton, OH (US); Rajan Keshav Panandiker, West Chester, OH (US); Kenneth Edward Yelm, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 65 days.

(21) Appl. No.: 13/528,114

(22) Filed: Jun. 20, 2012

(65) Prior Publication Data
US 2012/0323032 A1 Dec. 20, 2012

Related U.S. Application Data

(60) Provisional application No. 61/498,934, filed on Jun. 20, 2011.

(51) Int. Cl.
*C07F 7/18* (2006.01)
*C07F 7/10* (2006.01)
*C07C 213/00* (2006.01)

(52) U.S. Cl.
USPC ............ 556/425; 564/475; 564/476; 564/477

(58) Field of Classification Search
USPC .......................................................... 556/425
See application file for complete search history.

(56) References Cited

U.S. PATENT DOCUMENTS

| | | | | |
|---|---|---|---|---|
| 4,083,872 A * | 4/1978 | Schwarze et al. | ............. | 564/507 |
| 5,087,688 A | 2/1992 | Gruber et al. | | |
| 7,645,518 B2 * | 1/2010 | Hupfield | ........................ | 428/447 |

FOREIGN PATENT DOCUMENTS

WO WO 2005/052030 A1 6/2005

OTHER PUBLICATIONS

International Search Report; International Application No. PCT/US2012/043208; date of mailing Sep. 24, 2012; 10 pages.

* cited by examiner

*Primary Examiner* — Brian J Davis
(74) *Attorney, Agent, or Firm* — James F. McBride; Steven W. Miller

(57) ABSTRACT

The present application relates to molecules comprising one or more beta-hydroxyamine moieties, for example, aminosilicones and compositions such as consumer products comprising such molecules, as well as processes for making and using such molecules and such compositions. The aforementioned process is safer, more efficient and thus more economical. Thus, the aforementioned moleculers may be more widely used.

15 Claims, No Drawings

PROCESS OF MAKING β-HYDROXYAMINO COMPOUNDS

CROSS-REFERENCE TO RELATED APPLICATION(S)

This application claims priority under 35 U.S.C. §119(e) to U.S. Provisional Application Ser. No. 61/498,934, filed Jun. 20, 2011.

FIELD OF INVENTION

The present application relates to the synthesis of molecules comprising one or more β-hydroxyamine moieties, for example, β-hydroxyaminosilicones and compositions such as consumer products comprising such molecules.

BACKGROUND OF THE INVENTION

Molecules comprising one or more β-hydroxyamine moieties, include, but are not limited to, poly(β-hydroxyamino)silicones, poly(glycidylamino)silicones, poly(β-hydroxyvinylamines) and poly(β-hydroxyethylenimines). Such polymers are used in premium consumer products for benefits such as softness, hand, anti-wrinkle, hair conditioning/frizz control, color protection, etc. Unfortunately, molecules comprising a β-hydroxyamine moiety, including current aminosilicones, are expensive, difficult to produce requiring long reaction time, large reactors and high temperature during the reaction process. Current technologies for producing molecules comprising one or more β-hydroxyamine moieties are typically expensive and/or difficult to process due processing conditions and limited processing efficiencies. Thus, what is needed is an economical, safe technology for producing molecules comprising one or more beta-hydroxyamine moieties.

Applicants previously disclosed the use of certain protic solvents in the production of aminosilicones. Unfortunately, the process of making such β-hydroxyaminosilicones was not as efficient and therefore not as economical as desired. Applicants recognized that the source of the inefficiency and cost was that the current protic solvents did not have a sufficient number of the correct type of hydroxyl groups in the required proximity of the groups to each other. In short, Applicants recognized that as the hydroxy equivalent/gram of a protic solvent increases, the catalytic activity of the protic solvent increases, that primary and/or secondary hydroxyl moieties provide better catalytic activity than tertiary hydroxyl moieties, that as the proximity of such hydroxyl groups in the protic solvent molecule increases, the catalytic activity of the protic solvent increases and that as the solubility of the protic solvents in the amine feedstock decreases the catalytic activity of the protic solvent decreases. Thus, if a protic solvent is judiciously selected such that it has sufficient solubility in the amine feedstock, contains at least two hydroxyl moieties, preferably at least one of the moieties being a primary and/or secondary hydroxyl moiety, contains the maximum number of hydroxy equivalents/g and such hydroxyl equivalents are in the maximum proximity, for example alpha-beta proximity, alpha-gamma proximity or alpha-delta proximity, the process efficiency can be dramatically improved. A further benefit of such discovery is that flash point of such judiciously selected protic solvents is typically higher. Thus, the safety of the process is improved. This increase in safety decreases costs, as explosion proof processing equipment and transportation equipment/procedures may not be not required. Applicants recognized that the aforementioned benefits not only applied to the production of aminosilicones but to any molecule that comprises one or more one or more beta-hydroxyamine moieties.

Thus, Applicants disclose certain highly effective, economical processes for producing molecules that comprise one or more one or more beta-hydroxyamine moieties, for example aminosilicones, as well as the use of such molecules.

SUMMARY OF THE INVENTION

The present application relates to molecules comprising one or more beta-hydroxyamine moieties, for example, aminosilicones and compositions such as consumer products comprising such molecules, as well as processes for making and using such molecules and such compositions.

DETAILED DESCRIPTION OF THE INVENTION

Definitions

As used herein "consumer product" means baby care, beauty care, fabric & home care, family care, feminine care, health care, products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

As used herein the term "siloxyl residue" means a polydimethylsiloxane moiety.

As used herein, "substituted" means that the organic composition or radical to which the term is applied is:

(a) made unsaturated by the elimination of elements or radical; or
(b) at least one hydrogen in the compound or radical is replaced with a moiety containing one or more (i) carbon, (ii) oxygen, (iii) sulfur, (iv) nitrogen or (v) halogen atoms; or
(c) both (a) and (b).

Moieties that may replace hydrogen as described in (b) immediately above, which contain only carbon and hydrogen atoms are all hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Specific non-limiting examples of such groups are:

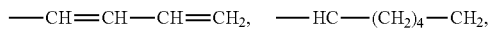

—φCH₃, —φCH₂φ, -φ, and -φ-φ.

Moieties containing oxygen atoms that may replace hydrogen as described in (b) immediately above include hydroxy, acyl or keto, ether, epoxy, carboxy, and ester containing groups. Specific non-limiting examples of such oxygen containing groups are:

—CH₂OH, —CCH₃CH₃OH, —CH₂COOH, —C(O)—(CH₂)₈CH₃, —OCH₂CH₃, =O, —OH, —CH₂—O—CH₂CH₃, —CH₂—O—(CH₂)₂—OH, —CH₂CH₂COOH, —φOH, —φOCH₂CH₃, —φCH₂OH,

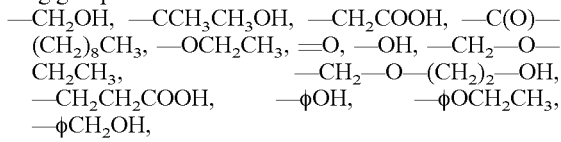

Moieties containing sulfur atoms that may replace hydrogen as described in (b) immediately above include the sulfur-containing acids and acid ester groups, thioether groups, mercapto groups and thioketo groups. Specific non-limiting examples of such sulfur containing groups are: —SCH₂CH₃, —CH₂S(CH₂)₄CH₃, —SO₃CH₂CH₃, SO₂CH₂CH₃, —CH₂COSH, —SH, —CH₂SCO, —CH₂C(S)CH₂CH₃, —SO₃H, —O(CH₂)₂C(S)CH₃, =S,

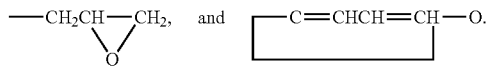

Moieties containing nitrogen atoms that may replace hydrogen as described in (b) immediately above include amino groups, the nitro group, azo groups, ammonium groups, amide groups, azido groups, isocyanate groups, cyano groups and nitrile groups. Specific non-limiting examples of such nitrogen containing groups are: —NHCH₃, —NH₂, —NH₃⁺, —CH₂CONH₂, —CH₂CON₃, —CH₂CH₂CH=NOH, —CN, —CH(CH₃)CH₂NCO, —CH₂NCO, —Nφ, —φN=NφOH, and =N.

Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety. Specific non-limiting examples of such halogen containing groups are: —(CH₂)₃COCl, —φF₅, —φCl, —CF₃, and —CH₂φBr.

It is understood that any of the above moieties that may replace hydrogen as described in (b) can be substituted into each other in either a monovalent substitution or by loss of hydrogen in a polyvalent substitution to form another monovalent moiety that can replace hydrogen in the organic compound or radical.

As used herein "φ" represents a phenyl ring.

As used herein, the nomenclature $SiO_{n/2}$ represents the ratio of oxygen and silicon atoms. For example, $SiO_{1/2}$ means that one oxygen is shared between two Si atoms Likewise $SiO_{2/2}$ means that two oxygen atoms are shared between two Si atoms and $SiO_{3/2}$ means that three oxygen atoms are shared are shared between two Si atoms.

As used herein random means that the $[(R_4Si(X—Z)O_{2/2}]$, $[R_4R_4SiO_{2/2}]$ and $[R_4SiO_{3/2}]$ units are randomly distributed throughout the polymer chain.

As used herein blocky means that multiple units of $[(R_4Si(X—Z)O_{2/2}]$, $[R_4R_4SiO_{2/2}]$ and $[R_4SiO_{3/2}]$ units are placed end to end throughout the polymer chain.

When a moiety or an indice of a preferred embodiment is not specifically defined, such moiety or indice is as previously defined.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Molecules Comprising β-hydroxyamine Moieties:

Suitable β-hydroxyamino compounds made by the aforementioned process include those which comprise one or more —N—CH(R)—CH(R)OH groups wherein each R is independently selected from the group consisting of H, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, $C_6$-$C_{32}$ substituted alkylaryl. In one aspect, said —N—CH(R)—CH(R)OH groups are attached to a polymeric molecule. In another aspect, the polymeric molecule is a siloxane polymer. Suitable organosilicone polymers that can be made by the aforementioned process are alkylated aminosilicones. In one aspect, these silicones include aminosilicones alkylated with alkylene oxide. In yet another aspect, suitable β-hydroxyalkyl siloxane polymers that can be synthesized using this invention include those selected from the group consisting of (i) a random or blocky β-hydroxyaminosilicone polymer having the following formula:
$[R_1R_2R_3SiO_{1/2}]_{(J+2)}[R_4Si(X—Z)O_{2/2}]_k[R_4R_4SiO_{2/2}]_m[R_4SiO_{3/2}]_j$ Wherein:
j is an integer from 0 to about 98; in one aspect j is an integer from 0 to about 48; in one aspect, j is 0;
k is an integer from 0 to about 200, in one aspect, k is an integer from 0 to about 50; when k=0, at least one of $R_1$, $R_2$ or $R_3$ is —X—Z;
m is an integer from 4 to about 5,000; in one aspect m is an integer from about 10 to about 4,000; in another aspect m is an integer from about 50 to about 2,000;
$R_1$, $R_2$, and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, and X—Z;

each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy;

each X in said alkyl siloxane polymer comprises a substituted or unsubstituted divalent alkylene radical comprising 2-12 carbon atoms, in one aspect each divalent alkylene radical is independently selected from the group consisting of —$(CH_2)_s$- wherein s is an integer from about 2 to about 8, or from about 2 to about 4; in one aspect, each X in said alkyl siloxane polymer comprises a substituted divalent alkylene radical selected from the group consisting of: —$CH_2$—CH(OH)—$CH_2$—; —$CH_2$—$CH_2$—CH(OH)—; and

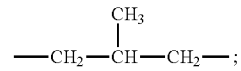

each Z is selected independently from the group consisting of

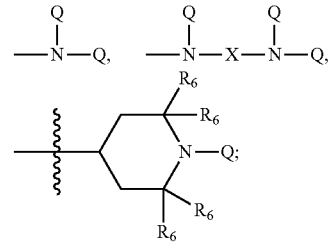

and at least one Q in said β-hydroxyaminosilicone is independently selected from —$CH_2$—CH(OH)—$CH_2$—$R_5$;

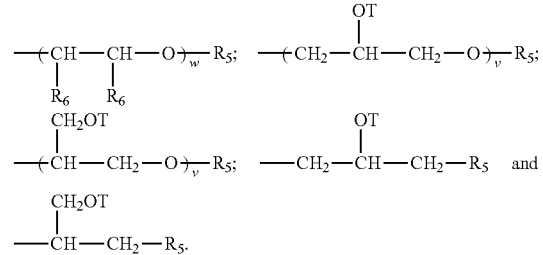

each additional Q in said β-hydroxyaminosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, —$CH_2$—CH(OH)—$CH_2$—$R_5$;

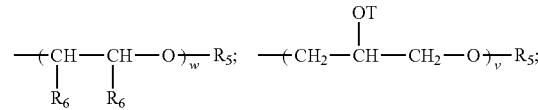

-continued

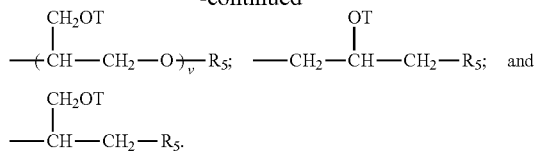

wherein each $R_5$ is independently selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl or $C_6$-$C_{32}$ alkylaryl, $C_6$-$C_{32}$ substituted alkylaryl, —(CHR$_6$—CHR$_6$—O—)$_w$-L and a siloxyl residue;

each $R_6$ is independently selected from H, $C_1$-$C_{18}$ alkyl each L is independently selected from —C(O)—$R_7$ or $R_7$;

w is an integer from 0 to about 500, in one aspect w is an integer from about 1 to about 200, one aspect w is an integer from about 1 to about 50;

each $R_7$ is selected independently selected from the group consisting of H; $C_1$-$C_{32}$ alkyl; $C_1$-$C_{32}$ substituted alkyl; $C_5$-$C_{32}$ or $C_6$-$C_{32}$ aryl; $C_5$-$C_{32}$ or $C_6$-$C_{32}$ substituted aryl; $C_6$-$C_{32}$ alkylaryl and $C_6$-$C_{32}$ substituted alkylaryl and a siloxyl residue;

each T is independently selected from H, and

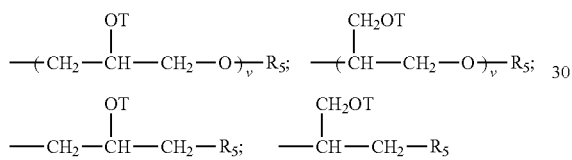

wherein each v in said organosilicone is an integer from 1 to about 20, in one aspect, v is an integer from 1 to about 10 and the sum of all v indices in each Q in said organosilicone is an integer from about 1 to about 30, from about 1 to about 20, or even from about 1 to about 10;

In one aspect, the β-hydroxyaminosilicones may be terminal organosilicones (organosilicones wherein the Z groups when present are present at the ends of the organosilicone's molecular chain) wherein $R_1$ and $R_2$ are each independently selected from the group consisting of H, OH, $C_1$-$C_{32}$ alkyl, in one aspect methyl, and $C_1$-$C_{32}$ alkoxy, in one aspect —OCH$_3$ or —OC$_2$H$_5$; and $R_1$ is —X—Z, k=0 and j is an integer from 0 to about 48.

In the second aspect, such terminal β-hydroxyaminosilicone may have the following structures:

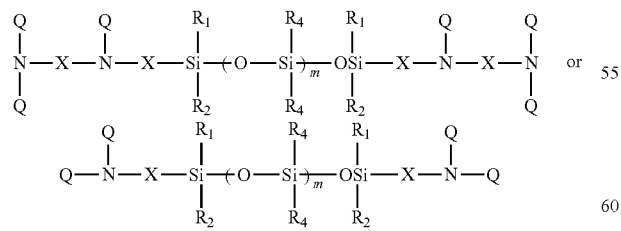

$R_1$ and $R_2$ are each independently selected from $C_1$-$C_{32}$ alkyl and $C_1$-$C_{32}$ alkoxy groups. In one aspect the aforementioned terminal organosiloxanes at least one Q in the β-hydroxyaminosilicone is selected from the group consisting of —CH$_2$—CH(OH)—CH$_2$—R$_5$;

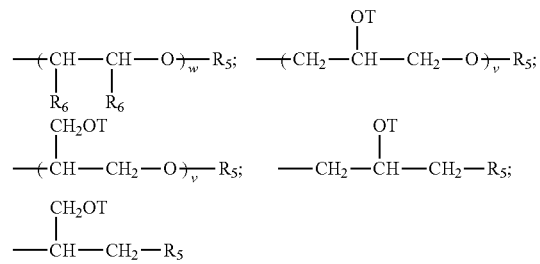

and each additional Q in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl; —CH$_2$—CH(OH)—CH$_2$—R$_5$;

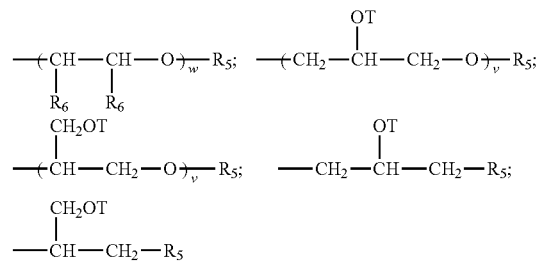

wherein each v in the said organosilicone is an integer selected from 1 to about 10 and the sum of all the v indices in each Q in the said organosilicone is an integer from about 1 to 30, from 1 to about 20 and even from 1 to about 10; all other indices and moieties are as previously described.

Process of Making

Protic solvents may be used as a catalytic solvent. Protic solvents are solvents that have a hydrogen atom bonded to an electronegative atom, yielding highly polarized bonds in which the hydrogen has protonlike character and can have hydrogen bonding characteristics. It is recognized that certain selected protic solvents are particularly effective at increasing the rate of the reaction.

Thus, a process of making one or more molecules comprising one or more beta-hydroxyamine moieties said process comprising:

a) combining one or more molecules comprising one or more primary and/or secondary amine moieties, with one or more molecules comprising one or more epoxide moieties and a catalyst comprising a protic solvent, said protic solvent:
   (i) having a hydroxyl equivalents of at least 0.007 equivalents per gram, from about 0.007 to about 0.032 equivalents per gram, from about 0.009 to about 0.026 equivalents per gram; from about 0.013 to about 0.022 equivalents per gram; and
   (ii) comprising at least two hydroxyl moieties per protic solvent molecule, and solubility of at least 0.2%, at least 0.3% to about 20%, or from about 0.5% to about 20% by weight of protic solvent in the mixture at the conditions of the reaction, to form a first mixture;

b) heating said first mixture to a temperature of from about 20° C. to about 200° C., from about 60° C. to about 175° C., or from about 100° C. to about 160° C. and maintaining said temperature for a time of from about 10 seconds to about 48 hours, from about 10 minutes to about 48 hours, from about 10 minutes to about 20 hours, from about 10 minutes to about 12 hours, from about 10 minutes to about 6 hours to form a composition comprising one or more molecules comprising one or more beta-hydroxyamine moieties; and c) optionally purifying said composition comprising one or more molecules comprising one or more beta-hydroxyamine moieties is disclosed.

In one aspect of said process, said protic solvent's at least two hydroxyl moieties per protic solvent molecule, have at least one conformation selected from the group consisting of α-β, α-γ, and α-δ.

In one aspect of said process, said protic solvent's at least two hydroxyl moieties per protic solvent molecule, have at least one conformation that is α-β.

In one aspect of said process, said protic solvent comprises two or three hydroxyl moieties per protic solvent molecule.

In one aspect of said process, said protic solvent has a flash point of at least 50° C., or from 100° C. to about 200° C.

In one aspect of said process, said composition comprising one or more molecules comprising one or more beta-hydroxyamine moieties comprises an organomodified silicone comprising one or more beta-hydroxyamine moieties.

In one aspect of said process, said composition comprising one or more molecules comprising one or more beta-hydroxyamine moieties does not comprise a silicone moiety, and wherein said protic solvent is not water.

In one aspect of said process, said protic solvent is selected from the group consisting of diols, triols, polyols, water, a water/surfactant mixture and mixtures thereof.

In one aspect of said process, said diol is selected from the group consisting of ethylene glycol, 1,2-propanediol, 1,3-propanediol, 2-methyl-1,3-propanediol, 2,2-dibutyl-1,3-propanediol, 2,2-diethyl-1,3-propanediol, 2-methylene-1,3-propanediol, 3-ethoxy-1,2-propanediol, 2-methyl-2-propyl-1,3-propanediol, 3-methoxy-1,2-propanediol, 1,2-butanediol, 1,3-butanediol, 1,4-butanediol, 2,3-butanediol, 1,2-pentanediol, 1,4-pentanediol, 1,5-pentanediol, 2,4-pentanediol, 1,2-hexanediol, neopentyl glycol, 1,5-hexanediol, 1,6-hexanediol, 2,5-hexanediol, 1,7-heptanediol, 1,4-heptanediol, 2-hydroxymethyl-1,3-propanediol, 1,2-octanediol, 1,8-octanediol, 4,5-octanediol, 1,9-nonanediol, 1,10-decanediol, 1,2-decanediol, 1,2-dodecanediol, 1,12-dodecanediol, 1,14-tetradecanediol, 1,2-tetradecanediol, 1,16-hexadecanediol, 1,2-hexadencanediol, 1,2-octadecanediol, 1,18-octadecanediol, and glycerol monoethers and mixtures thereof.

In one aspect of said process, said glycerol monoethers are selected from the group consisting of 3-propoxypropane-1, 2-diol, batyl alcohol and mixtures thereof.

In one aspect of said process, said triol is selected from the group consisting of glycerol, ethoxylated glycerol, propoxylated glycerol, alkoxyated glycerol, 1,1,1-tris(hydroxymethyl)ethane, 1,1,1-tris(hydroxymethyl)propane, 2-hydroxymethyl-1,3-propanediol, 1,2,4-butanetriol, 1,2,4-butanetriol, 3-methyl-1,3,5-pentanetriol, 1,2,3-hexanetriol, 1,2,6-hexanetriol, 1,2,3-heptanetriol, 1,2,3-octanetriol and mixtures thereof.

In one aspect of said process, said polyol is selected from the group consisting of pentaerythritol, alkoxylated pentaerythritol, sorbitol, alkoxylated sorbitol, glucose, alkoxylated glucose, fructose, alkoxylated fructoses, and mixtures thereof.

In one aspect of said process, said:
a) alkoxylated pentaerythritol is selected from the group consisting of ethoxylated pentaerythritol, proxylated pentaerythritol, and mixtures thereof;

b) alkoxylated sorbitol is selected from the group consisting of ethoxylated sorbitol, proxylated sorbitol and mixtures thereof;

c) alkoxylated glucose is selected from the group consisting of ethoxylated glucose, proxylated glucose, and mixtures thereof;

d) alkoxylated fructose is selected from the group consisting of ethoxylated fructose, proxylated fructose and mixtures thereof;

e) and mixtures thereof.

In one aspect of said process, said polyol is selected from the group consisting of a sugar, a carbohydrate, an alkoxylated sugar, an alkoxylated carbohydrate and mixtures thereof.

In one aspect of said process, said one or more molecules comprising one or more primary and/or secondary amine moieties comprises an amino silicone.

In one aspect of said process, said amino silicone is selected from the group consisting of an aminopropylmethylsiloxane-dimethylsiloxane copolymer, aminoethylaminopropylmethylsiloxane-dimethylsiloxane copolymer, aminoethylaminopropyl terminated polydimethylsiloxane, aminopropyl terminated polydimethylsiloxane and mixtures thereof.

In one aspect, an additional catalyst may be combined with the aminosilicone and the epoxide, the catalyst being used to react the epoxide with the aminosilicone. This reaction may optionally take place in a solvent. Suitable solvents include any solvent that is not reactive to the epoxide and that solubilizes the reagents, e.g., toluene, dichloromethane, tetrahydrofuran (THF). For example, an aminosilicone may be combined with an epoxide to form a first mixture. The first mixture may then be dissolved in toluene and a catalyst may be added to the mixture dissolved in toluene.

In addition to the protic solvent catalyst, additional catalysts may be used. Suitable catalysts for making the β-hydroxyamino silicones include, but are not limited to, metallic catalysts. The term "metallic catalyst" includes within its definition catalysts which include a metallic component. This definition includes metallic salts and materials such as $AlCl_3$, covalent compounds, and materials such as $BF_3$ and $SnCl_4$, all of which include a metallic component. The metallic component includes all elements commonly known as metals, such as alkali metals, alkaline earth metals, transition metals, and boron.

Suitable catalysts include, but are not limited to, $TiCl_4$, $Ti(OiPr)_4$, $ZnCl_2$, $SnCl_4$, $SnCl_2$, $FeCl_3$, $AlCl_3$, $BF_3$, platinum dichloride, copper(II) chloride, phosphorous pentachloride, phosphorous trichloride, cobalt(II) chloride, zinc oxide, iron (II) chloride and $BF_3$—$OEt_2$ and mixtures thereof. In some aspects, the metallic catalysts are Lewis acids. The metallic components of these Lewis acid catalysts include Ti, Zn, Fe, Sn, B, and Al. Suitable Lewis acid catalysts include $TiCl_4$, $SnCl_4$, $BF_3$, $AlCl_3$, and mixtures thereof. In some aspects, the catalyst is $SnCl_4$ or $TiCl_4$. The metallic Lewis acid catalysts may be employed at concentrations of about 0.1 mol % to about 5.0 mol %, in some aspects, about 0.2 mol % to about 1.0 mol %, in some aspects about 0.25 mol %.

Other suitable catalysts for making the β-hydroxyaminosilicone include basic or alkaline catalysts. The term "basic catalyst" includes within its definition catalysts which are basic or alkaline. This definition includes alkaline salts and materials such as KH, KOH, KOtBu, NaOEt, covalent compounds, and elements, such as metallic sodium.

Suitable catalysts include alkali metal alkoxylates, such as KOtBu, NaOEt, KOEt, NaOMe and mixtures thereof, NaH, NaOH, KOH, CaO, CaH, $Ca(OH)_2$, $Ca(OCH(CH_3)_2)_2$, Na and mixtures thereof. In some aspects, the catalyst is selected from alkali metal alkoxylates. In some aspects, the basic catalyst is a Lewis base. Suitable Lewis base catalysts include KOH, NaOCH$_3$, NaOC$_2$H$_5$, KOtBu, NaOH, and mixtures thereof. The Lewis base catalysts may be employed at concentrations of about 0.1 mol % to about 5.0 mol %, in some aspects, about 0.2 mol % to about 1.0 mol %. The alkali metal alkoxylate catalysts may be employed at concentrations of about 2.0 mol % to about 20.0 mol %, in some aspects, about 5.0 mol % to about 15.0 mol %.

In one aspect, suitable β-hydroxyamino silicones are produced by reacting terminal aminosilicones such as Structure A

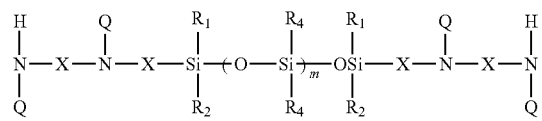

with an epoxide with the structure

to produce the organosilicone

Structure B

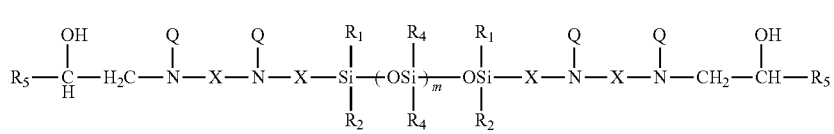

It is recognized that the epoxide can react with one or more than one N—H group in the aminosilicone (i.e. Q=hydrogen in structure A) to produce branched structures Structure C

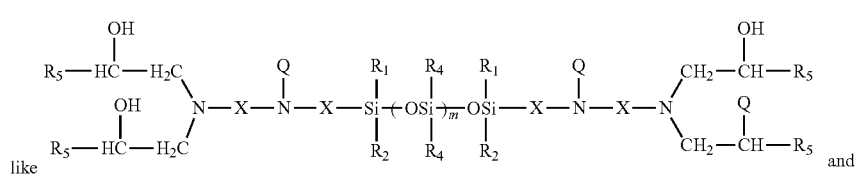

like and

Structure D

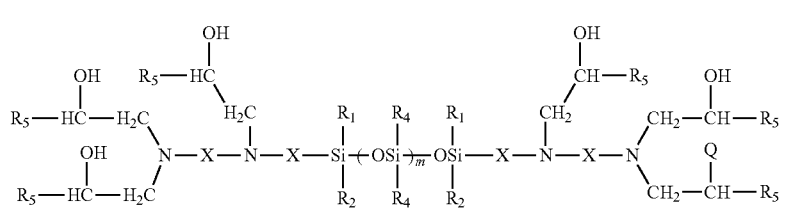

It is also recognized that not all the amine N—H groups must react with the epoxide.

Those skilled in the art will recognize that organomodified silicones analogous to structures B, C and D, can be made by reacting an aminosilicone of the structure Structure E

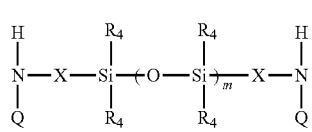

with an epoxide of the structure

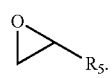

In one aspect, suitable β-hydroxyamino silicones are produced by reacting terminal aminosilicones such as Structure F

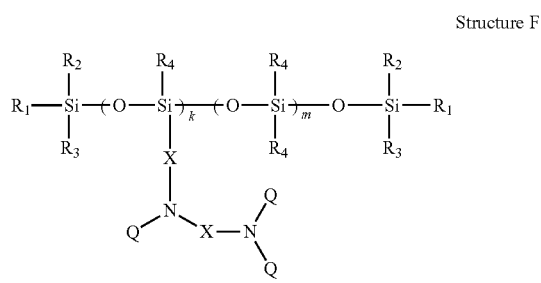

with an epoxide with the structure

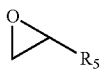

to produce the organosilicone

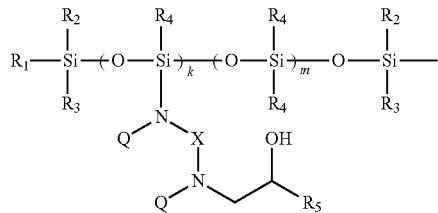

Structure G

It is recognized that the epoxide can react with one or more than one N—H group in the aminosilicone (i.e. Q=hydrogen in structure F) to produce branched structures like

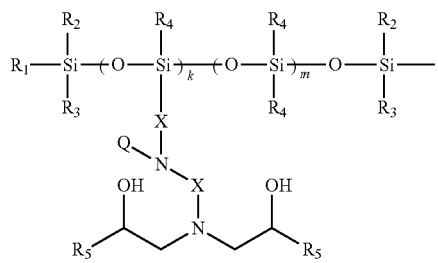

Structure H

And

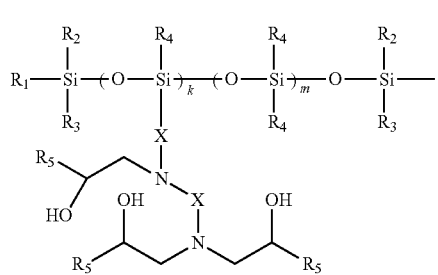

Structure I

It is also recognized that not all the amine N—H groups must react with the epoxide.

Those skilled in the art will recognize that β-hydroxyaminosilicone analogous to structures G, H and I, can be made by reacting an aminosilicone of the structure

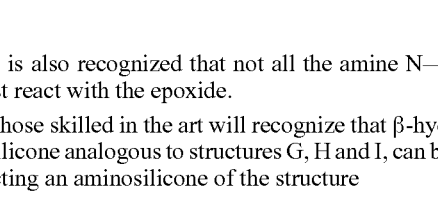

Structure J with an epoxide of the structure

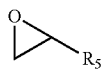

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Examples 1-23 are Examples of Making the β-hydroxyaminosilicones of the Present Invention

Example 1

Protic Solvent is 2-Propanol

A 600-milliliter Parr reactor is used (Model Number 4563 with 2 each pitched blade impellers, 4-blades each, 1.38" dia.). 100.0 grams of Shin-Etsu KF-8675 aminosilicone (available from Shin-Etsu Silicones of America Inc., Akron, Ohio) is mixed with 5.0 grams of 2-propanol and is drawn into the reactor using vacuum. The reactor is purged of air using vacuum and nitrogen cycles then charged with 5.5 grams of propylene oxide with stirring at 700 rpm (used throughout). The reactor is charged with nitrogen to ~90 psig and heated to 125° C. The reaction is allowed to run and samples are taken during the course of the reaction for later analysis. After 22 hours, the reactor is cooled and the product is drained to recover a clear and colorless mixture. The viscosity of the final mixture is 1750 centipoise. The samples are analyzed by NMR for % reaction of propylene oxide with the amino groups on the polymer.

Example 2

Protic Solvent is 1,2-Hexanediol

The general procedure is repeated from Example #1 using 100.0 grams of Shin-Etsu KF-8675 aminosilicone (available from Shin-Etsu Silicones of America Inc., Akron, Ohio) mixed with 5.0 grams of 1,2-hexanediol then reacted with 5.5 grams of propylene oxide at 125° C. while periodically taking several samples during the course of the reaction for later analysis. The viscosity of the final mixture after 15 hours of reaction time is 1450 centipoise and is clear and colorless. The samples are analyzed by NMR for % reaction of propylene oxide with the amino groups on the polymer.

Example 3

Protic Solvent is Hexylene Glycol

The general procedure is repeated from Example #1 using 100.0 grams of Shin-Etsu KF-8675 aminosilicone (available from Shin-Etsu Silicones of America Inc., Akron, Ohio) mixed with 5.0 grams of hexylene glycol then reacted with 5.5 grams of propylene oxide at 125° C. while taking several samples during the course of the reaction for later analysis. The viscosity of the final mixture after 21 hours of reaction time is 2200 centipoise and is clear and colorless. The samples are analyzed by NMR for % reaction of propylene oxide with the amino groups on the polymer.

Example 4

5-Gallon Reactor—Protic Solvent is 1,2-Hexanediol

A 5-Gallon Parr reactor is used (Model Number 4555 with 2 each pitched blade impellers, 6-blades each, 5.25" dia.) and is charged with 14053 grams of Shin-Etsu KF-8675 aminosilicone (available from Shin-Etsu Silicones of America Inc., Akron, Ohio) followed by 779 grams of 1,2-hexanediol. The reactor is purged of air using vacuum and nitrogen cycles then heated to 125° C. with stirring at 400 rpm (used throughout). The reactor is then charged with 759 grams of propylene oxide and is then charged with nitrogen to ~90 psig. The reaction is allowed to run while taking several samples during the course of the reaction for later analysis. After 8 hours, 106 grams of ethanolamine is added to the reactor to react with residual propylene oxide. The reactor is cooled to 100° C. and allowed to stir overnight. The next day, the reactor is cooled and the product is drained to recover a clear and colorless mixture. The viscosity of the final mixture is 2880 centipoise. The samples are analyzed by NMR for % reaction of propylene oxide with the amino groups on the polymer.

Example 5

Protic Solvent is 1,2-Propanediol

The general procedure is repeated from Example #1 using 100.0 grams of Shin-Etsu KF-8675 aminosilicone (available from Shin-Etsu Silicones of America Inc., Akron, Ohio) mixed with 3.2 grams of 1,2-propanediol then reacted with 5.5 grams of propylene oxide at 125° C. while periodically taking several samples during the course of the reaction for later analysis. The viscosity of the final mixture after 21 hours of reaction time is 3450 centipoise and is clear and colorless. The samples are analyzed by NMR for % reaction of propylene oxide with the amino groups on the polymer.

Example 6

Protic Solvent is 1,2-Butanediol

The general procedure is repeated from Example #1 using 100.0 grams of Shin-Etsu KF-8675 aminosilicone (available from Shin-Etsu Silicones of America Inc., Akron, Ohio) mixed with 3.7 grams of 1,2-butanediol then reacted with 5.5 grams of propylene oxide at 125° C. while periodically taking several samples during the course of the reaction for later analysis. The viscosity of the final mixture after 21 hours of reaction time is 1570 centipoise and is clear and colorless. The samples are analyzed by NMR for % reaction of propylene oxide with the amino groups on the polymer.

Example 7

Protic Solvent is 1,3-Butanediol

The general procedure is repeated from Example #1 using 100.0 grams of Shin-Etsu KF-8675 aminosilicone (available from Shin-Etsu Silicones of America Inc., Akron, Ohio) mixed with 3.7 grams of 1,3-butanediol then reacted with 5.5 grams of propylene oxide at 125° C. while periodically taking several samples during the course of the reaction for later analysis. The viscosity of the final mixture after 21 hours of reaction time is 2820 centipoise and is cloudy and colorless. The samples are analyzed by NMR for % reaction of propylene oxide with the amino groups on the polymer.

Example 8

Protic Solvent is 1,4-Butanediol

The general procedure is repeated from Example #1 using 100.0 grams of Shin-Etsu KF-8675 aminosilicone (available from Shin-Etsu Silicones of America Inc., Akron, Ohio) mixed with 3.7 grams of 1,4-butanediol then reacted with 5.5 grams of propylene oxide at 125° C. while periodically taking several samples during the course of the reaction for later analysis. The viscosity of the final mixture after 21 hours of reaction time is 2140 centipoise and is cloudy and colorless. The samples are analyzed by NMR for % reaction of propylene oxide with the amino groups on the polymer.

Example 9

Protic Solvent is Dipropylene Glycol

The general procedure is repeated from Example #1 using 100.0 grams of Shin-Etsu KF-8675 aminosilicone (available from Shin-Etsu Silicones of America Inc., Akron, Ohio) mixed with 5.6 grams of dipropylene glycol then reacted with 5.5 grams of propylene oxide at 125° C. while periodically taking several samples during the course of the reaction for later analysis. The viscosity of the final mixture after 21 hours of reaction time is 1690 centipoise and is clear and colorless. The samples are analyzed by NMR for % reaction of propylene oxide with the amino groups on the polymer.

Example 10

Protic Solvent is Neodol 25-1.8+Water

The general procedure is repeated from Example #1 using 100.0 grams of Shin-Etsu KF-8675 aminosilicone (available from Shin-Etsu Silicones of America Inc., Akron, Ohio) mixed with 5.0 grams of Neodol 25-1.8 and 2.5 grams of water then reacted with 5.5 grams of propylene oxide at 125° C. while periodically taking several samples during the course of the reaction for later analysis. The viscosity of the final mixture after 21 hours of reaction time is 520 centipoise and is cloudy and colorless. The samples are analyzed by NMR for % reaction of propylene oxide with the amino groups on the polymer.

Example 11

Protic Solvent is Neopentyl Glycol

The general procedure is repeated from Example #1 using 100.0 grams of Shin-Etsu KF-8675 aminosilicone (available from Shin-Etsu Silicones of America Inc., Akron, Ohio) mixed with 4.3 grams of neopentyl glycol then reacted with 5.5 grams of propylene oxide at 125° C. while periodically taking several samples during the course of the reaction for later analysis. The viscosity of the final mixture after 21 hours of reaction time is 1160 centipoise and is clear and colorless.

The samples are analyzed by NMR for % reaction of propylene oxide with the amino groups on the polymer.

Example 12

Protic Solvent is Glycerol Propoxylate

The general procedure is repeated from Example #1 using 100.0 grams of Shin-Etsu KF-8675 aminosilicone (available from Shin-Etsu Silicones of America Inc., Akron, Ohio) mixed with 7.4 grams of glycerol propoxylate then reacted with 5.5 grams of propylene oxide at 125° C. while periodically taking several samples during the course of the reaction for later analysis. The viscosity of the final mixture after 21 hours of reaction time is 1690 centipoise and is cloudy and colorless. The samples are analyzed by NMR for % reaction of propylene oxide with the amino groups on the polymer.

Example 13

Protic Solvent is 1,2-Hexanediol

The general procedure is repeated from Example #1 using 100.0 grams of Shin-Etsu KF-8675 aminosilicone (available from Shin-Etsu Silicones of America Inc., Akron, Ohio) mixed with 5.0 grams of 1,2-hexanediol then reacted with 4.2 grams of ethylene oxide at 125° C.

Example 14

Protic Solvent is 2-propanol

The general procedure is repeated from Example #1 using 100.0 grams of Shin-Etsu KF-8675 aminosilicone (available from Shin-Etsu Silicones of America Inc., Akron, Ohio) mixed with 5.0 grams of 2-propanol then reacted with 4.2 grams of ethylene oxide at 125° C.

Example 15

Protic Solvent is 2-propanol

The general procedure is repeated from Example #1 using 100.0 grams of Shin-Etsu KF-8008 aminosilicone (available from Shin-Etsu Silicones of America Inc., Akron, Ohio) mixed with 5.0 grams of 2-propanol then reacted with 1.1 grams of propylene oxide at 125° C.

Examples 16

Protic Solvent is 1,2-hexanediol

The general procedure is repeated from Example #1 using 100.0 grams of Shin-Etsu KF-8008 aminosilicone (available from Shin-Etsu Silicones of America Inc., Akron, Ohio) mixed with 5.0 grams of 1,2-hexanediol then reacted with 1.1 grams of propylene oxide at 125° C.

Example 17

Protic Solvent is Methanol

The general procedure is repeated from Example #1 using 100.0 grams of Shin-Etsu KF-8675 aminosilicone (available from Shin-Etsu Silicones of America Inc., Akron, Ohio) mixed with 2.7 grams of methanol then reacted with 5.5 grams of propylene oxide at 125° C. while periodically taking several samples during the course of the reaction for later analysis. The viscosity of the final mixture after 21 hours of reaction time is 1750 centipoise and is clear and colorless. The samples are analyzed by NMR for % reaction of propylene oxide with the amino groups on the polymer.

Example 18

Protic Solvent is 1-Butanol

The general procedure is repeated from Example #1 using 100.0 grams of Shin-Etsu KF-8675 aminosilicone (available from Shin-Etsu Silicones of America Inc., Akron, Ohio) mixed with 6.2 grams of 1-butanol then reacted with 5.5 grams of propylene oxide at 125° C. while periodically taking several samples during the course of the reaction for later analysis. The viscosity of the final mixture after 21 hours of reaction time is 1390 centipoise and is clear and colorless. The samples are analyzed by NMR for % reaction of propylene oxide with the amino groups on the polymer.

Example 19

Protic Solvent is 2-Butanol

The general procedure is repeated from Example #1 using 100.0 grams of Shin-Etsu KF-8675 aminosilicone (available from Shin-Etsu Silicones of America Inc., Akron, Ohio) mixed with 6.2 grams of 2-butanol then reacted with 5.5 grams of propylene oxide at 125° C. while periodically taking several samples during the course of the reaction for later analysis. The viscosity of the final mixture after 21 hours of reaction time is 1500 centipoise and is clear and colorless. The samples are analyzed by NMR for % reaction of propylene oxide with the amino groups on the polymer.

Example 20

Protic Solvent is Tert-Butanol

The general procedure is repeated from Example #1 using 100.0 grams of Shin-Etsu KF-8675 aminosilicone (available from Shin-Etsu Silicones of America Inc., Akron, Ohio) mixed with 6.2 grams of tent-butanol then reacted with 5.5 grams of propylene oxide at 125° C. while periodically taking several samples during the course of the reaction for later analysis. The viscosity of the final mixture after 21 hours of reaction time is 1230 centipoise and is clear and colorless. The samples are analyzed by NMR for % reaction of propylene oxide with the amino groups on the polymer.

Example 21

Protic Solvent is 1,2-hexanediol

The general procedure is repeated from Example #1 using 16.2 grams of Epoxypropoxypropyl Terminated Polydimethylsiloxane DMS-E12 (available from Gelest, Inc.) mixed with 2.3 grams of 1,2-hexanediol then reacted with 30.00 grams of Poly(propylene glycol)bis(2-aminopropyl ether) 406686 (available from Sigma-Aldrich, St. Louis, Mo.) at 125° C.

Example 22

Monomethylamine/PO/TAS (where a Diol is Formed In-Situ; Process Simplification)

The general procedure is repeated from Example #1 using 100.0 grams of Shin-Etsu KF-8008 aminosilicone (available from Shin-Etsu Silicones of America Inc., Akron, Ohio) is added to the reactor then reacted with 1.0 gram of monomethylamine then 9.5 grams of propylene oxide at 125° C. This procedure forms 5 grams of N-Methyldiisopropanolamine in-situ and becomes the diprotic catalyst used in the reaction.

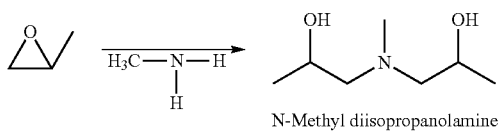

N-Methyl diisopropanolamine

Example 23

Ammonia/PO/TAS (where a Triol is Formed In-Situ; Process Simplification)

The general procedure is repeated from Example #1 using 100.0 grams of Shin-Etsu KF-8008 aminosilicone (available from Shin-Etsu Silicones of America Inc., Akron, Ohio) is added to the reactor then reacted with 0.44 grams of ammonia then 9.5 grams of propylene oxide at 125° C. This procedure forms 5 grams of Triisopropanolamine in-situ and becomes the triprotic catalyst used in the reaction.

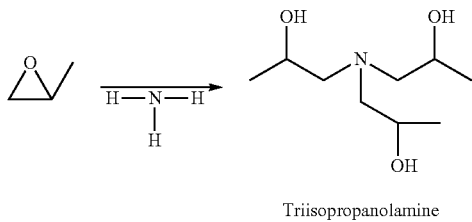

Triisopropanolamine

Example 24

Protic Solvent is 1,2,4-butanetriol

A 600-milliliter Parr reactor is used (Model Number 4563 with 2 each pitched blade impellers, 4-blades each, 1.38" dia.). 390 grams of Shin-Etsu KF-8675 aminosilicone (available from Shin-Etsu Silicones of America Inc., Akron, Ohio) is mixed with 11.7 grams of 1,2,4-butanetriol and is drawn into the reactor using vacuum. The reactor is purged of air using vacuum and nitrogen cycles then charged with nitrogen to ~90 psig and heated to 125° C. Then the reactor is charged with 22 grams of propylene oxide with stifling at 500 rpm (used throughout). The reaction is allowed to run and samples are taken during the course of the reaction for later analysis. After analysis shows that the reaction is complete, the reactor is cooled and the product is drained to recover a white opaque mixture. The samples are analyzed by titration to determine the remaining amount of primary and secondary amine.

Example 25

Protic Solvent is 1,2,6-hexanetriol

A 600-milliliter Parr reactor is used (Model Number 4563 with 2 each pitched blade impellers, 4-blades each, 1.38" dia.). 383 grams of Shin-Etsu KF-8675 aminosilicone (available from Shin-Etsu Silicones of America Inc., Akron, Ohio) is mixed with 14.6 grams of 1,2,6-hexanetriol and is drawn into the reactor using vacuum. The reactor is purged of air using vacuum and nitrogen cycles then charged with nitrogen to ~90 psig and heated to 125° C. Then the reactor is charged with 21 grams of propylene oxide with stifling at 500 rpm (used throughout). The reaction is allowed to run and samples are taken during the course of the reaction for later analysis. After analysis shows that the reaction is complete, the reactor is cooled and the product is drained to recover a white opaque mixture. The samples are analyzed by titration to determine the remaining amount of primary and secondary amine.

Example 26

Protic Solvent is 1,2-octanediol

A 600-milliliter Parr reactor is used (Model Number 4563 with 2 each pitched blade impellers, 4-blades each, 1.38" dia.). 392 grams of Shin-Etsu KF-8675 aminosilicone (available from Shin-Etsu Silicones of America Inc., Akron, Ohio) is mixed with 23.8 grams of 1,2-octanediol and is drawn into the reactor using vacuum. The reactor is purged of air using vacuum and nitrogen cycles then charged with nitrogen to ~90 psig and heated to 125° C. Then the reactor is charged with 23 grams of propylene oxide with stifling at 500 rpm (used throughout). The reaction is allowed to run and samples are taken during the course of the reaction for later analysis. After analysis shows that the reaction is complete, the reactor is cooled and the product is drained to recover a amber translucent mixture. The samples are analyzed by titration to determine the remaining amount of primary and secondary amine.

Example 27

Protic Solvent is 1,6-hexanediol

A 600-milliliter Parr reactor is used (Model Number 4563 with 2 each pitched blade impellers, 4-blades each, 1.38" dia.). 215 grams of Shin-Etsu KF-8675 aminosilicone (available from Shin-Etsu Silicones of America Inc., Akron, Ohio) is mixed with 10.6 grams of 1,6-hexanediol and is drawn into the reactor using vacuum. The reactor is purged of air using vacuum and nitrogen cycles then charged with nitrogen to ~90 psig and heated to 125° C. Then the reactor is charged with 23 grams of propylene oxide with stifling at 500 rpm (used throughout). The reaction is allowed to run and samples are taken during the course of the reaction for later analysis. After analysis shows that the reaction is complete, the reactor is cooled and the product is drained to recover a white opaque mixture. The samples are analyzed by titration to determine the remaining amount of primary and secondary amine.

Example 28

Protic Solvent is 1,2-dihydroxybenzene

A 600-milliliter Parr reactor is used (Model Number 4563 with 2 each pitched blade impellers, 4-blades each, 1.38" dia.). 373 grams of Shin-Etsu KF-8675 aminosilicone (available from Shin-Etsu Silicones of America Inc., Akron, Ohio) is mixed with 17.1 grams of 1,2-dihydroxybenzene and is drawn into the reactor using vacuum. The reactor is purged of air using vacuum and nitrogen cycles then charged with nitrogen to ~90 psig and heated to 125° C. Then the reactor is charged with 21 grams of propylene oxide with stifling at 500 rpm (used throughout). The reaction is allowed to run and samples are taken during the course of the reaction for later analysis. After analysis shows that the reaction is complete, the reactor is cooled and the product is drained to recover a brown opaque mixture. The samples are analyzed by NMR for % reaction of propylene oxide with the amino groups on the polymer.

The protic solvents listed in the table below were all tested at identical equivalents of hydroxyl group. Examples 3-8, 11, 23, and 25 represent protic solvents having multiple hydroxyl groups in close proximity. Examples 9 and 12 represent protic solvents having only multiple hydroxyl groups. Examples 1 and 17-20 represent protic solvents having single hydroxyl groups—thus no opportunity for close proximity exists. Examples 21-22, and 24 represent protic solvents having limited solubility in the amine feedstock.

| From Example No. | Protic Solvent | 4 hr % Conversion | >90% Conversion | Hydroxy Equiv./g |
|---|---|---|---|---|
| 3 | Hexylene glycol | — | 8 hr | 0.017 |
| 4 | 1,2-Hexanediol | 100 | 2.5 hr | 0.017 |
| 5 | 1,2-Propanediol | 80 | <8 hr | 0.026 |
| 6 | 1,2-Butanediol | — | <8 hr | 0.022 |
| 7 | 1,3-Butanediol | — | <8 hr | 0.022 |
| 8 | 1,4-Butanediol | — | <6 hr | 0.022 |
| 11 | Neopentyl glycol | 85 | <5 hr | 0.019 |
| 26 | 1,2-octanediol | 97 | 3 hrs | 0.014 |
| 28 | 1,2-dihydroxybenzene | >95 | 2.5 hrs | 0.018 |
| 9 | Dipropylene glycol | 59 | 21 hr | 0.015 |
| 12 | Glyceryl propoxylate (Mn = 266) | — | 21 hr | 0.011 |
| 1 | 2-Propanol | 79 | 21 hr | 0.017 |
| 17 | Methanol | 56 | >21 hr | 0.031 |
| 18 | 1-Butanol | 65 | 21 hr | 0.013 |
| 19 | 2-Butanol | 54 | >21 hr | 0.013 |
| 20 | Tert-butanol | 51 | 21 hr | 0.013 |
| 24 | 1,2,4-butanetriol* | 52 | 21 hrs | 0.028 |
| 25 | 1,2,6-hexanetriol* | 55 | 21 hrs | 0.022 |
| 27 | 1,6-hexanediol* | 72 | 7.5 hrs | 0.017 |

*protic solvent having limited solubility in the amine feedstock

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of making one or more molecules comprising one or more beta-hydroxyamine moieties said process comprising:

a) combining one or more molecules comprising one or more primary and/or secondary amine moieties, said one or more molecules comprising an amino silicone, with one or more molecules comprising one or more epoxide moieties and a catalyst comprising a protic solvent, said protic solvent:
  (i) having a hydroxyl equivalents of at least 0.007 equivalents per gram; and
  (ii) comprising at least two hydroxyl moieties per protic solvent molecule, and solubility of at least 0.2% by weight of protic solvent in the mixture at the conditions of the reaction, to form a first mixture;

b) heating said first mixture to a temperature of from about 20° C. to about 200° C., and maintaining said temperature for a time of from about 10 seconds to about 48 hours, to form a composition comprising one or more molecules comprising one or more beta-hydroxyamine moieties; and c) optionally purifying said composition comprising one or more molecules comprising one or more beta-hydroxyamine moieties.

2. The process of claim 1 wherein said protic solvent's at least two hydroxyl moieties per protic solvent molecule, have at least one conformation selected from the group consisting of α-β, α-γ, and α-δ.

3. The process of claim 1 wherein said protic solvent's at least two hydroxyl moieties per protic solvent molecule, have at least one conformation that is α-β.

4. The process of claim 1 wherein said protic solvent comprises two or three hydroxyl moieties per protic solvent molecule.

5. The process of claim 1 wherein said protic solvent has a flash point of at least 50° C.

6. The process of claim 1 wherein said composition comprising one or more molecules comprising one or more beta-hydroxyamine moieties comprises an organomodified silicone comprising one or more beta-hydroxyamine moieties.

7. The process of claim 1 wherein said protic solvent is selected from the group consisting of diols, triols, polyols and mixtures thereof.

8. The process of claim 7 wherein the said diol is selected from the group consisting of ethylene glycol, 1,2-propanediol, 1,3-propanediol, 2-methyl-1,3-propanediol, 2,2-dibutyl-1,3-propanediol, 2,2-diethyl-1,3-propanediol, 2-methylene-1,3-propanediol, 3-ethoxy-1,2-propanediol, 2-methyl-2-propyl-1,3-propanediol, 3-methoxy-1,2-propanediol, 1,2-butanediol, 1,3-butanediol, 1,4-butanediol, 2,3-butanediol, 1,2-pentanediol, 1,4-pentanediol, 1,5-pentanediol, 2,4-pentanediol, 1,2-hexanediol, neopentyl glycol, 1,5-hexanediol, 1,6-hexanediol, 2,5-hexanediol, 1,7-heptanediol, 1,4-heptanediol, 2-hydroxymethyl-1,3-propanediol, 1,2-octanediol, 1,8-octanediol, 4,5-octanediol, 1,9-nonanediol, 1,10-decanediol, 1,2-decanediol, 1,2-dodecanediol, 1,12-dodecanediol, 1,14-tetradecanediol, 1,2-tetradecanediol, 1,16-hexadecanediol, 1,2-hexadecanediol, 1,2-octadecanediol, 1,18-octadecanediol, and glycerol monoethers and mixtures thereof.

9. The process of claim 8 wherein the said glycerol monoethers are selected from the group consisting of 3-propoxypropane-1,2-diol, batyl alcohol and mixtures thereof.

10. The process of claim 7 wherein the said triol is selected from the group consisting of glycerol, ethoxylated glycerol, propoxylated glycerol, alkoxyated glycerol, 1,1,1-tris(hydroxymethyl)ethane, 1,1,1-tris(hydroxymethyl)propane, 2-hydroxymethyl-1,3-propanediol, 1,2,4-butanetriol, 1,2,4- butanetriol, 3-methyl-1,3,5-pentanetriol, 1,2,3-hexanetriol, 1,2,6-hexanetriol, 1,2,3-heptanetriol, 1,2,3-octanetriol and mixtures thereof.

11. The process of claim 7 wherein the said polyol is selected from the group consisting of pentaerythritol, alkoxylated pentaerythritol, sorbitol, alkoxylated sorbitol, glucose, alkoxylated glucose, fructose, alkoxylated fructoses, and mixtures thereof.

12. The process of claim 11 wherein the said:
   a) alkoxylated pentaerythritol is selected from the group consisting of ethoxylated pentaerythritol, proxylated pentaerythritol, and mixtures thereof;
   b) alkoxylated sorbitol is selected from the group consisting of ethoxylated sorbitol, proxylated sorbitol and mixtures thereof;
   c) alkoxylated glucose is selected from the group consisting of ethoxylated glucose, proxylated glucose, and mixtures thereof;
   d) alkoxylated fructose is selected from the group consisting of ethoxylated fructose, proxylated fructose and mixtures thereof.

13. The process of claim 7 wherein the said polyol is selected from the group consisting of a sugar, a carbohydrate, an alkoxylated sugar, an alkoxylated carbohydrate and mixtures thereof.

14. The process of claim 1 wherein said amino silicone is selected from the group consisting of an aminopropylmethylsiloxane-dimethylsiloxane copolymer, aminoethylaminopropylmethylsiloxane-dimethylsiloxane copolymer, aminoethylaminopropyl terminated polydimethylsiloxane, aminopropyl terminated polydimethylsiloxane and mixtures thereof.

15. A process of making one or more molecules comprising one or more beta-hydroxyamine moieties said process comprising:
   a) combining one or more molecules comprising one or more primary and/or secondary amine moieties, said one or more molecules comprising an amino silicone, with one or more molecules comprising one or more epoxide moieties and a catalyst comprising a protic solvent, said protic solvent being selected from the group consisting of diols, a water/diol mixture, triols, a water/triol mixture, polyols, a water/polyol mixture, a water/surfactant mixture and mixtures thereof;
   b) heating said first mixture to a temperature of from about 20° C. to about 200° C., and maintaining said temperature for a time of from about 10 seconds to about 48 hours, to form a composition comprising one or more molecules comprising one or more beta-hydroxyamine moieties; and
   c) optionally purifying said composition comprising one or more molecules comprising one or more beta-hydroxyamine moieties.

* * * * *